United States Patent
Kanou et al.

(10) Patent No.: US 7,709,676 B2
(45) Date of Patent: May 4, 2010

(54) METHOD FOR PRODUCING PURIFIED 2-CYANOACRYLATE

(75) Inventors: Muneaki Kanou, Aichi (JP); Yoshiharu Ohashi, Aichi (JP)

(73) Assignee: Toagosei Co., Ltd., Tokyo (JP)

( * ) Notice: Subject to any disclaimer, the term of this patent is extended or adjusted under 35 U.S.C. 154(b) by 1191 days.

(21) Appl. No.: 10/558,382

(22) PCT Filed: May 27, 2004

(86) PCT No.: PCT/JP2004/007653

§ 371 (c)(1),
(2), (4) Date: Nov. 29, 2005

(87) PCT Pub. No.: WO2004/106284

PCT Pub. Date: Dec. 9, 2004

(65) Prior Publication Data

US 2007/0027335 A1    Feb. 1, 2007

(30) Foreign Application Priority Data

May 30, 2003    (JP) ............................. 2003-154892

(51) Int. Cl.
*C07C 255/11*    (2006.01)
(52) U.S. Cl. ...................................................... 558/443
(58) Field of Classification Search ................. 558/443
See application file for complete search history.

(56) References Cited

U.S. PATENT DOCUMENTS

| 2,794,788 A | 6/1957 | Coover, Jr. et al. |
| 3,728,373 A | 4/1973 | Imohel et al. |
| 4,986,884 A * | 1/1991 | Arlt et al. ...................... 203/8 |
| 6,602,970 B2 * | 8/2003 | Ando et al. ................. 526/298 |

FOREIGN PATENT DOCUMENTS

| DE | 20 27 502 A1 | 12/1971 |
| JP | 46-37278 B1 | 11/1971 |
| JP | 48-85531 A | 11/1973 |
| JP | 49-31619 A | 3/1974 |
| JP | 1-135754 A | 5/1989 |
| JP | 4-124168 A | 4/1992 |
| JP | 10-182580 A | 7/1998 |

OTHER PUBLICATIONS

Supplementary European Search Report dated Nov. 26, 2007.

* cited by examiner

*Primary Examiner*—James O Wilson
*Assistant Examiner*—Ebenezer Sackey
(74) *Attorney, Agent, or Firm*—Sughrue Mion, PLLC

(57) ABSTRACT

A method for producing a purified 2-cyanoacrylate is characterized in that distillation is conducted in the presence of a polymerization inhibitor whose boiling point is within ±12° C. of the boiling point of the 2-cyanoacrylate. With this method, polymerization of 2-cyanoacrylate can be continuously prevented in the distillate system during distillation of a crude 2-cyanoacrylate, so that a purified 2-cyanoacrylate can be obtained.

11 Claims, No Drawings

METHOD FOR PRODUCING PURIFIED 2-CYANOACRYLATE

TECHNICAL FIELD

The present invention relates to a method for producing a purified 2-cyanoacrylate, which is widely used as a main component of an instant adhesive and, in particular, to an improvement in a purification step of the production process.

BACKGROUND ART

A 2-cyanoacrylate is generally produced by condensation of a cyanoacetate and formaldehyde in an organic solvent, followed by depolymerization of the polymer thus obtained at high temperature and reduced pressure. A crude 2-cyanoacrylate obtained here generally has low purity, poor adhesion performance, poor stability, etc., and it is therefore further distilled to give a purified 2-cyanoacrylate.

With regard to distillation and purification of a 2-cyanoacrylate, a method is known in which, in order to prevent polymerization of the 2-cyanoacrylate, an anionic polymerization inhibitor such as diphosphorus pentoxide, phosphoric acid, or paratoluenesulfonic acid, and a radical polymerization inhibitor such as hydroquinone, catechol, or pyrogallol are added to a crude 2-cyanoacrylate, which is then subjected to distillation at reduced pressure while heating.

Furthermore, JP-A-1-135754 (JP-A denotes a Japanese unexamined patent application publication) proposes a method in which distillation is carried out while continuously and countercurrently adding a polymerization inhibitor from an upper part of a distillation column.

Moreover, U.S. Pat. No. 2,794,788 discloses a method in which distillation is carried out under a flow of an acidic gas such as $SO_2$, $BF_3$, HF, or $CO_2$, for the purpose of inhibiting polymerization of a 2-cyanoacrylate in a distillate system.

Furthermore, JP-A-4-124168 proposes a method in which distillation is carried out without using the above-mentioned acidic gas but instead using a polymerization inhibitor such as a $BF_3$ ether complex salt or a $BF_3$ carboxylic acid complex salt.

DISCLOSURE OF INVENTION

However, even if the above-mentioned polymerization inhibitor such as diphosphorus pentoxide or hydroquinone, or the polymerization inhibitor such as a $BF_3$ ether complex salt or a $BF_3$ carboxylic acid complex salt is used, there is still the problem that the 2-cyanoacrylate easily polymerizes in the distillate system.

Furthermore, with regard to the method in which distillation is carried out under a flow of an acidic gas such as $SO_2$, $BF_3$, HF, or $CO_2$, since a 2-cyanoacrylate thus obtained contains a large amount of acidic gas, it is necessary to remove this acidic gas by degassing, etc. Moreover, since these acidic gases are discharged as exhaust gas, removal equipment is necessary, and there are problems in terms of the operation and the environment.

It is an object of the present invention to solve the above-mentioned problems, that is, to provide a method that, unlike the case in which an acidic gas is used, does not have problems in terms of the operation and the environment, and that can continuously prevent a 2-cyanoacrylate from polymerizing in the distillate system when distilling the 2-cyanoacrylate.

As a result of an intensive investigation in order to attain this object by the present inventors into a method of preventing polymerization of a 2-cyanoacrylate in the distillate system when distilling it, the present invention has been accomplished. That is, the present invention is a method for producing a purified 2-cyanoacrylate by distilling a crude 2-cyanoacrylate in the presence of a polymerization inhibitor, characterized in that a polymerization inhibitor having a boiling point at normal pressure of within ±12° C. of the boiling point at normal pressure of the purified 2-cyanoacrylate is used as the polymerization inhibitor.

BEST MODE FOR CARRYING OUT THE INVENTION

The present inventors have found that the polymerization inhibitor used in JP-A-1-135754 has a boiling point that is higher than the boiling point of ethyl 2-cyanoacrylate by more than 12° C., and when a polymerization inhibitor having a boiling point that is higher than the boiling point of a 2-cyanoacrylate by more than 12° C. is used, the 2-cyanoacrylate easily polymerizes in the distillate system. When the reason therefor was investigated, it was found that, although the use of such a polymerization inhibitor can prevent polymerization in a distillation column for which its use is targeted, since the polymerization inhibitor, as a vapor, does not accompany the 2-cyanoacrylate, it cannot spread to the distillate system.

Furthermore, it has been found that the polymerization inhibitor used in JP-A-4-124168 has a boiling point that is lower than the boiling point of a 2-cyanoacrylate by more than 12° C., as is the case for a $BF_3$ ether complex salt or a $BF_3$ carboxylic acid complex salt, or has a boiling point that is higher than the boiling point of a 2-cyanoacrylate by more than 12° C., as is the case for a $BF_3$ phenol complex salt, and when a polymerization inhibitor having a boiling point that is lower than the boiling point of a 2-cyanoacrylate by more than 12° C. is used, polymerization can easily occur in the distillate system in the latter half of the distillation during long term distillation. When the reason therefor was investigated, it was found that such a polymerization inhibitor separates in an initial stage of the distillation and goes out of the system. The present invention has been accomplished on the basis of the above-mentioned findings.

The present invention is explained in further detail below.

Examples of the 2-cyanoacrylate in the present invention include methyl 2-cyanoacrylate, ethyl 2-cyanoacrylate, propyl 2-cyanoacrylate, isopropyl 2-cyanoacrylate, butyl 2-cyanoacrylate, isobutyl 2-cyanoacrylate, amyl 2-cyanoacrylate, hexyl 2-cyanoacrylate, cyclohexyl 2-cyanoacrylate, octyl 2-cyanoacrylate, 2-ethylhexyl 2-cyanoacrylate, allyl 2-cyanoacrylate, benzyl 2-cyanoacrylate, methoxyethyl 2-cyanoacrylate, ethoxyethyl 2-cyanoacrylate, methoxypropyl 2-cyanoacrylate, and tetrahydrofurfuryl 2-cyanoacrylate, and these 2-cyanoacrylates may be used not only singly but also in a combination of two or more types.

The boiling points of these 2-cyanoacrylates at normal pressure are for example 195° C. for methyl 2-cyanoacrylate, 200° C. for ethyl 2-cyanoacrylate, 205° C. for isopropyl 2-cyanoacrylate, and 210° C. for isobutyl 2-cyanoacrylate.

The polymerization inhibitor used in the present invention has a boiling point at normal pressure that is within ±12° C. of the boiling point at normal pressure of a given purified 2-cyanoacrylate, and preferably within ±10° C. The actual distillation of a 2-cyanoacrylate is often carried out at reduced pressure. The difference in boiling point between compounds decreases under reduced pressure, but since the difference varies according to the degree of reduced pressure, in the present invention the boiling points at normal pressure are used as the basis. As long as the above-mentioned conditions are satisfied, the polymerization inhibitor used in the present invention may be a radical polymerization inhibitor, but an anionic polymerization inhibitor is preferable.

Examples of the anionic polymerization inhibitor (figures in brackets are based on the boiling point at normal pressure) include, with respect to ethyl 2-cyanoacrylate (200° C.), chloroacetic acid (189° C.), dichloroacetic acid (194° C.), trichloroacetic acid (196° C.), bromoacetic acid (206° C.), dibromofluoroacetic acid (198° C.), 3-chloropropionic acid (203-205° C.), 2,2-dichloropropionic acid (210° C.), 2-bromopropionic acid (203° C.), 2-chlorobutyric acid (210° C.), 4-chlorobutyric acid (196° C.), tert-butylacetic acid (190° C.), 2,3-dimethylbutyric acid (191-192° C.), 2-ethylbutyric acid (191-195° C.), 2-ethyl-2-methylbutyric acid (200-202° C.), 3-methoxyisobutyric acid (197-201° C.), 2-methylvaleric acid (196-197° C.), 3-methylvaleric acid (196-198° C.), 4-methylvaleric acid (199-201° C.), 2-ethylvaleric acid (209° C.), 2-methoxyvaleric acid (193-197° C.), hexanoic acid (202° C.), 5-hexenoic acid (202° C.), 3,3-dimethylacrylic acid (194-195° C.), pentafluoropropanesulfonic acid (196° C.), a $BF_3$ methanol complex (200° C.), and a $BF_3$ ethanol complex (200° C.).

Furthermore, examples thereof include, with respect to propyl 2-cyanoacrylate (210° C.), bromoacetic acid, 3-chloropropionic acid, 2,2-dichloropropionic acid, 2-bromopropionic acid, 3-ethoxypropionic acid (216° C.), 3-ethoxy-2-methylpropionic acid (214-215° C.), 2-chlorobutyric acid, 2-ethyl-2-methylbutyric acid, 3-methoxyisobutyric acid, 2-methoxymethylbutyric acid (218-220° C.), 2-ethylvaleric acid, 2-ethyl-4-methylvaleric acid (218-220° C.), 2-propylvaleric acid (220° C.), hexanoic acid, 2-methylhexanoic acid (209° C.), 5-methylhexanoic acid (212° C.), 5-hexenoic acid, nonafluorobutanesulfonic acid (210-212° C.), a $BF_3$ methanol complex, and a $BF_3$ ethanol complex.

Moreover, examples thereof include, with respect to butyl 2-cyanoacrylate (230° C.), 3-methylsulfanylpropionic acid (235-240° C.), 2,2-diethylbutyric acid (220-221° C.), 2-methoxymethylbutyric acid, 2-ethoxymethylbutyric acid (225-226° C.), 3,4-dimethylvaleric acid (220-225° C.), 2-ethyl-4-methylvaleric acid, 2-propylvaleric acid, 5-oxovaleric acid (240° C.), 2,5-dimethylhexanoic acid (228-230° C.), heptanoic acid (223° C.), 3-ethylheptanoic acid (236° C.), octanoic acid (237° C.), cyclohexanecarboxylic acid (232-233° C.), trichloroacrylic acid (221-223° C.), cyanoacetic acid (230° C.), undecafluoropentanesulfonic acid (223-226° C.), and tridecafluorohexanesulfonic acid.

Furthermore, examples thereof include, with respect to ethoxyethyl 2-cyanoacrylate (240° C.), 3-methylsulfanylpropionic acid, 5-oxovaleric acid, 2,5-dimethylhexanoic acid, 3-ethylheptanoic acid, 2-methoxyheptanoic acid (246-250° C.), octanoic acid, 2-methyloctanoic acid (244-246° C.), cyclohexanecarboxylic acid, and cyanoacetic acid.

Among these polymerization inhibitors, since those having a high acidity are fast-acting at low concentration, a halocarboxylic acid or a halosulfonic acid is preferable. Specific examples thereof include chloroacetic acid, dichloroacetic acid, trichloroacetic acid, bromoacetic acid, dibromofluoroacetic acid, 3-chloropropionic acid, 2,2-dichloropropionic acid, 2-bromopropionic acid, 2-chlorobutyric acid, 4-chlorobutyric acid, pentafluoropropanesulfonic acid, nonafluorobutanesulfonic acid, trichloroacrylic acid, undecafluoropentanesulfonic acid, tridecafluorohexanesulfonic acid, and 3-methylsulfanylpropionic acid. Furthermore, if the relationship to the boiling point of a 2-cyanoacrylate is satisfied, dichloroacetic acid and trichloroacetic acid are particularly preferable. Moreover, other than the halocarboxylic acids and halosulfonic acids, a $BF_3$ methanol complex and a $BF_3$ ethanol complex are preferable.

These boiling points can be looked up in a catalogue such as Aldrich or a chemical database called 'CrossFire Beilstein'.

With regard to the crude 2-cyanoacrylate used in the present invention, a crude 2-cyanoacrylate that can be obtained by a standard method in which, for example, a cyanoacetic acid ester and formaldehyde are heated and condensed in an organic solvent in the presence of a basic catalyst, and the condensate thus obtained is depolymerized at reduced pressure and high temperature in the presence of a depolymerization catalyst and a polymerization inhibitor, may generally be used.

With regard to a distillation method, there is, for example, a method in which the crude 2-cyanoacrylate produced by the above-mentioned method is heated at reduced pressure using a packed distillation column or a plate-type distillation column. During this process, the distillation pressure is preferably 1 to 10 mmHg, and the distillation temperature is preferably 50° C. to 100° C. Furthermore, during this process, it is preferable to add, to the crude 2-cyanoacrylate in the vessel, an anionic polymerization inhibitor such as diphosphorus pentoxide, paratoluenesulfonic acid, methanesulfonic acid, or propanesultone or a radical polymerization inhibitor such as hydroquinone, t-butylcatechol, or pyrogallol, and it is more preferable to add both thereof. Since these polymerization inhibitors are added for stabilization of a vessel solution, it is preferable to use one having a boiling point that is higher than the boiling point of a target 2-cyanoacrylate by more than 12° C. The amounts of anionic polymerization inhibitor and radical polymerization inhibitor having boiling points that are higher than the boiling point of the 2-cyanoacrylate by more than 12° C. are preferably 0.05 to 1.0 parts by weight for either of the polymerization inhibitors relative to the 2-cyanoacrylate (100 parts by weight).

With regard to a method of adding a polymerization inhibitor having a boiling point that is within ±12° C., and preferably ±10° C., of the boiling point of a 2-cyanoacrylate, it may be added to a crude 2-cyanoacrylate in a vessel in advance, or it may be dissolved in a purified 2-cyanoacrylate and added to a distillation vessel or continuously added via an upper part of a distillation column. It is preferable that the polymerization inhibitor is added to the vessel and continuously added via the upper part of the distillation column.

The polymerization inhibitor is preferably added in an amount of 1 to 1000 wt ppm relative to the crude or purified 2-cyanoacrylate, and more preferably 10 to 100 wt ppm. If the polymerization inhibitor is in the above-mentioned range, it exhibits a sufficient effect as a polymerization inhibitor, there is no possibility that it might undergo polymerization within the distillate system, and the adhesion speed of the fraction obtained can be maintained at the intended speed.

It is preferable for the purpose of storage to add to the distilled purified 2-cyanoacrylate an appropriate amount of an anionic polymerization inhibitor such as $SO_2$, paratoluenesulfonic acid, methanesulfonic acid, propanesultone, or a $BF_3$ complex, or a radical polymerization inhibitor such as hydroquinone, t-butylcatechol, or pyrogallol.

It is surmised that the reason why, in the distillation of a 2-cyanoacrylate, polymerization in the distillate system can be prevented if a polymerization inhibitor having a boiling point that is close to that of the 2-cyanoacrylate is used is because this polymerization inhibitor accompanies the 2-cyanoacrylate vapor to thus spread evenly from the distillation column to the distillate system, and polymerization can therefore be prevented throughout the distillation equipment over a long period of time.

EXAMPLES

The present invention is explained in further detail by reference to Examples and Comparative Examples, but the present invention is not limited thereby. As an evaluation method, the presence or absence of a polymer in the distillate system was visually examined.

Examples 1 to 6 and Comparative Examples 1 to 4

Hydroquinone (0.5 wt %) and diphosphorus pentoxide (0.1 wt %) were added to crude ethyl 2-cyanoacrylate as vessel solution stabilizers, the mixture was refluxed using a packed distillation column having a theoretical number of plates of 10 at a reduced pressure of 5 mmHg and at a vessel temperature of 70° C. to 80° C. for 1 hour while continuously spraying a purified ethyl 2-cyanoacrylate solution of a compound shown in Table 1 as a polymerization inhibitor (the concentration being shown in Table 1) from an upper part of the packed column, then distilled at a reflux ratio of 3. After an initial fraction of 10% was distilled away, a fraction of 60% to 70% of purified ethyl 2-cyanoacrylate was obtained. The presence or absence of polymerization in the distillate system is shown in Table 1.

Example 7

Hydroquinone (0.5 wt %) and diphosphorus pentoxide (0.1 wt %) were added to crude methyl 2-cyanoacrylate as vessel solution stabilizers, distillation was carried out in the same manner as in Example 1 except that a purified methyl 2-cyanoacrylate solution of a compound shown in Table 1 as a polymerization inhibitor (the concentration being shown in Table 1) was continuously sprayed from an upper part of the packed column, and purified methyl 2-cyanoacrylate was obtained. The presence or absence of polymerization in the distillate system is shown in Table 1.

Example 8

Hydroquinone (0.5 wt %) and diphosphorus pentoxide (0.1 wt %) were added to crude isopropyl 2-cyanoacrylate as vessel solution stabilizers, distillation was carried out in the same manner as in Example 1 except that a purified isopropyl 2-cyanoacrylate solution of a compound shown in Table 1 as a polymerization inhibitor (the concentration being shown in Table 1) was continuously sprayed from the top of the packed column and the vessel temperature was 80° C. to 90° C., and purified isopropyl 2-cyanoacrylate was obtained. The presence or absence of polymerization in the distillate system is shown in Table 1.

Example 9

Hydroquinone (0.5 wt %) and diphosphorus pentoxide (0.1 wt %) were added to crude isobutyl 2-cyanoacrylate as vessel solution stabilizers, distillation was carried out in the same manner as in Example 1 except that a purified isobutyl 2-cyanoacrylate solution of a compound shown in Table 1 as a polymerization inhibitor (the concentration being shown in Table 1) was continuously sprayed from an upper part of the packed column and the vessel temperature was 80° C. to 90° C., and purified isobutyl 2-cyanoacrylate was obtained. The presence or absence of polymerization in the distillate system is shown in Table 1.

TABLE 1

| | 2-Cyanoacrylate | | Polymerization inhibitor | | | Polymer in distillate system |
|---|---|---|---|---|---|---|
| | Type | Boiling point (° C.) | Type | Boiling point (° C.) | Amount added* | |
| Ex. 1 | Ethyl | 200 | Dichloroacetic acid | 194 | 50 | None |
| Ex. 2 | Ethyl | 200 | Dichloroacetic acid | 194 | 10 | None |
| Ex. 3 | Ethyl | 200 | Dichloroacetic acid | 194 | 100 | None |
| Ex. 4 | Ethyl | 200 | Trichloroacetic acid | 196 | 10 | None |
| Ex. 5 | Ethyl | 200 | Hexanoic acid | 202 | 100 | None |
| Ex. 6 | Ethyl | 200 | $BF_3$ methanol complex | 200 | 50 | None |
| Ex. 7 | Methyl | 195 | Dichloroacetic acid | 194 | 50 | None |
| Ex. 8 | Isopropyl | 205 | $BF_3$ methanol complex | 200 | 50 | None |
| Ex. 9 | Isobutyl | 210 | Bromoacetic acid | 206 | 100 | None |
| Comp. Ex. 1 | Ethyl | 200 | Paratoluenesulfonic acid | 260 | 50 | Yes (large amount) |
| Comp. Ex. 2 | Ethyl | 200 | 4-Methylhexanoic acid | 221 | 100 | Yes (large amount) |
| Comp. Ex. 3 | Ethyl | 200 | $BF_3$ diethyl ether complex | 126 | 50 | Yes (large amount) |
| Comp. Ex. 4 | Ethyl | 200 | $BF_3$ acetic acid complex | 180 | 50 | Yes (small amount) |

*ppm

As is clear from Table 1, when the polymerization inhibitor in accordance with the present invention was not used but a polymerization inhibitor having a boiling point that was higher than the boiling point of the 2-cyanoacrylate by more than 12° C. was instead added (Comparative Example 1 and 2), and when a polymerization inhibitor having a boiling point that was lower than the boiling point of the 2-cyanoacrylate by more than 12° C. was instead added (Comparative Example 3 and 4), a polymer deposit was observed on the distillate system during distillation. In contrast, when a polymerization inhibitor was continuously added by the method in accordance with the present invention (Examples 1 to 9), no polymer deposit was observed on the distillate system.

INDUSTRIAL APPLICABILITY

The present invention enables polymerization in a distillation column and a distillate system to be prevented continuously, even when distillation of a 2-cyanoacrylate is carried out for a long period of time, by carrying out distillation in the presence of a polymerization inhibitor having a boiling point that is within ±12° C. of the boiling point of the 2-cyanoacrylate. In accordance with the present invention, a purified 2-cyanoacrylate having a high purity can be obtained in one step by carrying out distillation using, for example, a multiplate distillation column or by increasing a reflux ratio.

What is claimed is:

1. A method for producing a purified 2-cyanoacrylate by distilling a crude 2-cyanoacrylate in the presence of a polymerization inhibitor, characterized in that an anionic polymerization inhibitor having a boiling point at normal pressure of within ±12° C. of the boiling point at normal pressure of the purified 2-cyanoacrylate is used as the polymerization inhibitor, wherein the anionic polymerization inhibitor is a halocarboxylic acid, a halosulfonic acid, a $BF_3$ methanol complex or a $BF_3$ ethanol complex, and wherein distillation is carried out by further adding, to a 2-cyanoacrylate in a vessel, an anionic polymerization inhibitor having a boiling point that is higher than the boiling point of the 2-cyanoacrylate by more than 12° C. and a radical polymerization inhibitor having a boiling point that is higher than the boiling point of the 2-cyanoacrylate by more than 12° C.

2. The production method according to claim 1, wherein the anionic polymerization inhibitor is a halocarboxylic acid or a halosulfonic acid.

3. The production method according to claim 2, wherein the halocarboxylic acid or the halosulfonic acid is chloroacetic acid, dichloroacetic acid, trichloroacetic acid, bromoacetic acid, dibromofluoroacetic acid, 3-chloropropionic acid, 2,2-dichloropropionic acid, 2-bromopropionic acid, 2-chlorobutyric acid, 4-chlorobutyric acid, pentafluoropropanesulfonic acid, nonafluorobutanesulfonic acid, trichloroacrylic acid, undecafluoropentanesulfonic acid, tridecafluorohexanesulfonic acid, or 3-methylsulfanylpropionic acid.

4. The production method according to claim 1, wherein the anionic polymerization inhibitor is a $BF_3$ methanol complex or a $BF_3$ ethanol complex.

5. The production method according to claim 1, wherein the polymerization inhibitor is added to a vessel in advance.

6. The production method according to claim 1, wherein the polymerization inhibitor is dissolved in a purified 2-cyanoacrylate and continuously added via an upper part of a distillation vessel or an upper part of a distillation column.

7. The production method according to claim 5, wherein the polymerization inhibitor is added at 1 to 1000 wt ppm relative to the crude 2-cyanoacrylate.

8. The production method according to claim 6, wherein the polymerization inhibitor is added at 1 to 1000 wt ppm relative to the crude 2-cyanoacrylate.

9. The production method according to claim 1, wherein a crude 2-cyanoacrylate obtained by heating and condensing a cyanoacetic acid ester and formaldehyde in an organic solvent in the presence of a basic catalyst, and depolymerizing the condensate thus obtained in the presence of a depolymerization catalyst and a polymerization inhibitor at reduced pressure and high temperature is used as the crude 2-cyanoacrylate.

10. The production method according to claim 1, wherein distillation employs a method in which heating is carried out at reduced pressure using a packed distillation column.

11. The production method according to claim 1, wherein the anionic polymerization inhibitor having a boiling point that is higher than the boiling point of the 2-cyanoacrylate by more than 12° C. is phosphorus pentoxide and the radical polymerization inhibitor having a boiling point that is higher than the boiling point of the 2-cyanoacrylate by more than 12° C. is hydroquinone.

* * * * *